(12) United States Patent
Carpentier et al.

(10) Patent No.: US 9,351,829 B2
(45) Date of Patent: May 31, 2016

(54) DOUBLE CROSS-LINKAGE PROCESS TO ENHANCE POST-IMPLANTATION BIOPROSTHETIC TISSUE DURABILITY

(75) Inventors: Sophie M. Carpentier, Paris (FR); Alain F. Carpentier, Paris (FR)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 13/297,192

(22) Filed: Nov. 15, 2011

(65) Prior Publication Data

US 2012/0123557 A1    May 17, 2012

Related U.S. Application Data (60) Provisional application No. 61/414,726, filed on Nov. 17, 2010.

(51) Int. Cl.
- *A61F 2/24* (2006.01)
- *A61L 27/36* (2006.01)
- *A61K 35/34* (2015.01)

(52) U.S. Cl.
CPC .............. *A61F 2/2415* (2013.01); *A61K 35/34* (2013.01); *A61L 27/3625* (2013.01); *A61L 27/3687* (2013.01); *A61L 2400/02* (2013.01); *A61L 2430/20* (2013.01)

(58) Field of Classification Search
USPC .......................... 514/693; 8/94; 530/345, 350
See application file for complete search history.

(56) References Cited

U.S. PATENT DOCUMENTS

| | | | |
|---|---|---|---|
| 2,393,580 A | 1/1946 | Weiskopf | |
| 2,484,813 A | 10/1949 | Bower | |
| 2,567,929 A | 9/1951 | Fessenden | |
| 3,002,895 A | 10/1961 | Freedman | |
| 3,093,439 A | 6/1963 | Bothwell | |
| 3,870,789 A | 3/1975 | Mikat | |
| 3,927,422 A | 12/1975 | Sawyer | |
| 3,961,097 A | 6/1976 | Gravlee, Jr. | |
| 3,966,401 A | 6/1976 | Hancock et al. | |
| 4,050,893 A | 9/1977 | Hancock et al. | |
| 4,067,091 A | 1/1978 | Backman | |
| 4,082,507 A | 4/1978 | Sawyer | |
| 4,120,649 A | 10/1978 | Schechter | |
| 4,120,991 A | 10/1978 | Ornstein et al. | |
| 4,197,658 A | 4/1980 | Fraser | |
| 4,207,689 A | 6/1980 | Romera-Sierra et al. | |
| 4,294,753 A | 10/1981 | Urist | |
| 4,320,157 A | 3/1982 | von Hagens | |
| 4,323,358 A | 4/1982 | Lentz et al. | |
| 4,328,256 A | 5/1982 | Romero-Sierra et al. | |
| 4,347,671 A | 9/1982 | Dias et al. | |
| 4,350,492 A | 9/1982 | Wright et al. | |
| 4,372,743 A | 2/1983 | Lane | |
| 4,378,224 A | 3/1983 | Nimni et al. | |
| 4,402,697 A | 9/1983 | Pollock et al. | |
| 4,405,327 A | 9/1983 | Pollock | |
| 4,481,009 A | 11/1984 | Nashef | |
| 4,553,974 A | 11/1985 | Dewanjee | |
| 4,599,084 A | 7/1986 | Nashef | |
| 4,624,822 A | 11/1986 | Arru et al. | |
| 4,647,283 A | 3/1987 | Carpentier et al. | |
| 4,648,881 A | 3/1987 | Carpentier et al. | |
| 4,655,773 A | 4/1987 | Grassi | |
| 4,676,070 A | 6/1987 | Linner | |
| 4,729,139 A | 3/1988 | Nashef | |
| 4,753,652 A | 6/1988 | Langer et al. | |
| 4,770,665 A | 9/1988 | Nashef | |
| 4,776,853 A | 10/1988 | Klement et al. | |
| 4,786,287 A | 11/1988 | Nashef et al. | |
| 4,800,603 A | 1/1989 | Jaffe | |
| 4,831,065 A | 5/1989 | Pietsch et al. | |
| 4,838,888 A | 6/1989 | Nashef | |
| 4,865,871 A | 9/1989 | Livesey et al. | |
| 4,885,005 A | 12/1989 | Nashef et al. | |
| 4,891,319 A | 1/1990 | Roser | |
| 4,911,713 A | 3/1990 | Sauvage et al. | |
| 4,958,008 A | 9/1990 | Petite et al. | |
| 4,969,912 A | 11/1990 | Kelman et al. | |
| 4,975,526 A | 12/1990 | Kuberasampath et al. | |
| 4,976,733 A | 12/1990 | Girardot | |
| 4,990,131 A | 2/1991 | Dardik et al. | |
| 4,994,030 A | 2/1991 | Glowczewskie, Jr. et al. | |
| 4,994,237 A | 2/1991 | Login et al. | |
| 4,996,054 A | 2/1991 | Pietsch et al. | |
| 5,002,566 A | 3/1991 | Carpentier et al. | |

(Continued)

FOREIGN PATENT DOCUMENTS

| | | |
|---|---|---|
| WO | 84/01894 A1 | 5/1984 |
| WO | 95/11047 A1 | 4/1995 |
| WO | 95/22361 A1 | 8/1995 |
| WO | 95/34332 A1 | 12/1995 |
| WO | 96/04028 A1 | 2/1996 |

(Continued)

OTHER PUBLICATIONS

Jeffamine, Huntsman Group, 2008.*
Julien et al., Shelf-life of bioprosthetic heart valves: a structural and mechanical study, Biomaterials, 18, p. 605-612, 1997.*
Tween80, Sigma Product Sheet, 2014.*
Polyetheramine, Scienoc Product Sheet, 2014.*

(Continued)

*Primary Examiner* — Taeyoon Kim
*Assistant Examiner* — Srikanth Patury
(74) *Attorney, Agent, or Firm* — Michelle C. Kim; AnnMarie Kaiser; Pui Tong Ho (57) ABSTRACT

Bioprosthetic tissues and methods for making same, comprising fixing bioprosthetic implant tissue by treatment with 0.1 to 10 wt. % glutaraldehyde at elevated temperature, capping said fixed tissue by treatment with a diamine crosslinking agent, and treating said capped tissue with about 0.6 wt. % glutaraldehyde.

25 Claims, 7 Drawing Sheets

(56) References Cited

U.S. PATENT DOCUMENTS

| | | |
|---|---|---|
| 5,011,913 A | 4/1991 | Benedict et al. |
| 5,024,830 A | 6/1991 | Linner |
| 5,044,165 A | 9/1991 | Linner et al. |
| 5,051,401 A | 9/1991 | Sikes |
| 5,068,086 A | 11/1991 | Sklenak et al. |
| 5,068,100 A | 11/1991 | McClanahan |
| 5,080,670 A | 1/1992 | Imamura et al. |
| 5,094,661 A | 3/1992 | Levy et al. |
| 5,104,405 A | 4/1992 | Nimni |
| 5,108,923 A | 4/1992 | Benedict et al. |
| 5,116,564 A | 5/1992 | Jansen et al. |
| 5,131,908 A | 7/1992 | Dardik et al. |
| 5,147,514 A | 9/1992 | Mechanic |
| 5,149,621 A | 9/1992 | McNally et al. |
| 5,149,653 A | 9/1992 | Roser |
| 5,154,007 A | 10/1992 | Piunno et al. |
| 5,200,399 A | 4/1993 | Wettlaufer et al. |
| 5,215,541 A | 6/1993 | Nashef et al. |
| 5,275,954 A | 1/1994 | Wolfinbarger et al. |
| 5,279,612 A | 1/1994 | Eberhardt |
| 5,290,558 A | 3/1994 | O'Leary et al. |
| 5,296,583 A | 3/1994 | Levy |
| 5,332,475 A | 7/1994 | Mechanic |
| 5,336,616 A | 8/1994 | Livesey et al. |
| 5,368,608 A | 11/1994 | Levy et al. |
| 5,397,353 A | 3/1995 | Oliver et al. |
| 5,424,047 A | 6/1995 | Zwingenberger et al. |
| 5,436,291 A | 7/1995 | Levy et al. |
| 5,437,287 A | 8/1995 | Phillips et al. |
| 5,447,536 A | 9/1995 | Girardot et al. |
| 5,447,724 A | 9/1995 | Helmus et al. |
| 5,460,962 A | 10/1995 | Kemp |
| 5,476,516 A | 12/1995 | Seifter et al. |
| 5,507,813 A | 4/1996 | Dowd et al. |
| 5,509,932 A | 4/1996 | Keogh et al. |
| 5,556,379 A | 9/1996 | Wolfinbarger |
| 5,558,875 A | 9/1996 | Wang |
| 5,595,571 A | 1/1997 | Jaffe et al. |
| 5,613,982 A | 3/1997 | Goldstein |
| 5,632,778 A | 5/1997 | Goldstein |
| 5,645,587 A | 7/1997 | Chanda et al. |
| 5,674,298 A | 10/1997 | Levy et al. |
| 5,679,112 A | 10/1997 | Levy et al. |
| 5,695,820 A | 12/1997 | Davis et al. |
| 5,697,972 A | 12/1997 | Kim et al. |
| 5,720,777 A | 2/1998 | Jaffe et al. |
| 5,733,339 A | 3/1998 | Girardot et al. |
| 5,746,775 A | 5/1998 | Levy et al. |
| 5,762,600 A | 6/1998 | Bruchman et al. |
| 5,766,520 A | 6/1998 | Bronshtein |
| 5,769,780 A | 6/1998 | Hata et al. |
| 5,773,285 A | 6/1998 | Park |
| 5,776,182 A | 7/1998 | Bruchman et al. |
| 5,782,914 A | 7/1998 | Schankereli |
| 5,782,915 A | 7/1998 | Stone |
| 5,782,931 A | 7/1998 | Yang et al. |
| 5,792,603 A | 8/1998 | Dunkelman et al. |
| 5,843,180 A | 12/1998 | Jaffe et al. |
| 5,843,181 A | 12/1998 | Jaffe et al. |
| 5,843,182 A | 12/1998 | Goldstein |
| 5,855,620 A | 1/1999 | Bishopric et al. |
| 5,856,102 A | 1/1999 | Bierke-Nelson et al. |
| 5,856,172 A | 1/1999 | Greenwood et al. |
| 5,862,806 A | 1/1999 | Cheung |
| 5,865,849 A | 2/1999 | Stone |
| 5,873,812 A | 2/1999 | Ciana et al. |
| 5,879,383 A | 3/1999 | Bruchman et al. |
| 5,882,850 A | 3/1999 | Khor et al. |
| 5,882,918 A | 3/1999 | Goffe |
| 5,899,936 A | 5/1999 | Goldstein |
| 5,902,338 A | 5/1999 | Stone |
| 5,904,718 A | 5/1999 | Jefferies |
| 5,911,951 A | 6/1999 | Girardot et al. |
| 5,913,900 A | 6/1999 | Stone |
| 5,919,472 A | 7/1999 | Trescony et al. |
| 5,922,027 A | 7/1999 | Stone |
| 5,931,969 A | 8/1999 | Carpentier et al. |
| 5,935,168 A | 8/1999 | Yang et al. |
| 5,945,319 A | 8/1999 | Keogh |
| 5,977,153 A | 11/1999 | Camiener |
| 5,987,720 A | 11/1999 | Yamamoto |
| 5,993,844 A | 11/1999 | Abraham et al. |
| 6,008,292 A | 12/1999 | Lee et al. |
| 6,017,741 A | 1/2000 | Keogh |
| 6,024,735 A | 2/2000 | Wolfinbarger, Jr. |
| 6,063,120 A | 5/2000 | Stone |
| 6,066,160 A | 5/2000 | Colvin et al. |
| 6,093,204 A | 7/2000 | Stone |
| 6,093,530 A | 7/2000 | McIlroy et al. |
| 6,106,555 A | 8/2000 | Yang |
| 6,117,979 A | 9/2000 | Hendriks et al. |
| 6,121,041 A | 9/2000 | Mirsch, II et al. |
| 6,132,473 A | 10/2000 | Williams et al. |
| 6,132,986 A | 10/2000 | Pathak et al. |
| 6,156,531 A | 12/2000 | Pathak et al. |
| 6,166,184 A | 12/2000 | Hendriks et al. |
| 6,177,514 B1 | 1/2001 | Pathak et al. |
| 6,190,407 B1 | 2/2001 | Ogle et al. |
| 6,193,749 B1 | 2/2001 | Schroeder et al. |
| 6,203,755 B1 | 3/2001 | Odland |
| 6,206,917 B1 | 3/2001 | Williams et al. |
| 6,210,957 B1 | 4/2001 | Carpentier et al. |
| 6,214,054 B1 | 4/2001 | Cunanan et al. |
| 6,214,055 B1 | 4/2001 | Simionescu et al. |
| 6,231,608 B1 | 5/2001 | Stone |
| 6,231,614 B1 | 5/2001 | Yang |
| 6,251,579 B1 | 6/2001 | Moore et al. |
| 6,254,635 B1 | 7/2001 | Schroeder et al. |
| 6,258,320 B1 | 7/2001 | Persing et al. |
| 6,267,786 B1 | 7/2001 | Stone |
| 6,277,555 B1 | 8/2001 | Duran et al. |
| 6,287,338 B1 | 9/2001 | Sarnowski et al. |
| 6,290,991 B1 | 9/2001 | Roser et al. |
| 6,302,909 B1 | 10/2001 | Ogle et al. |
| 6,312,474 B1 | 11/2001 | Francis et al. |
| 6,322,593 B1 | 11/2001 | Pathak et al. |
| 6,322,994 B1 | 11/2001 | Reid |
| 6,328,762 B1 | 12/2001 | Anderson et al. |
| 6,352,708 B1 | 3/2002 | Duran et al. |
| 6,364,905 B1 | 4/2002 | Simpson et al. |
| 6,372,228 B1 | 4/2002 | Gregory |
| 6,375,680 B1 | 4/2002 | Carlyle |
| 6,376,244 B1 | 4/2002 | Atala |
| 6,383,732 B1 | 5/2002 | Stone |
| 6,391,538 B1 | 5/2002 | Vyavahare et al. |
| 6,394,096 B1 | 5/2002 | Constantz |
| 6,448,076 B2 | 9/2002 | Dennis et al. |
| 6,468,660 B2 | 10/2002 | Ogle et al. |
| 6,471,723 B1 | 10/2002 | Ashworth et al. |
| 6,479,079 B1 | 11/2002 | Pathak et al. |
| 6,506,339 B1 | 1/2003 | Girardot et al. |
| 6,509,145 B1 | 1/2003 | Torrianni |
| 6,527,979 B2 | 3/2003 | Constantz et al. |
| 6,531,310 B1 | 3/2003 | Mirsch, II et al. |
| 6,534,004 B2 | 3/2003 | Chen et al. |
| 6,547,827 B2 | 4/2003 | Carpentier et al. |
| 6,561,970 B1 | 5/2003 | Carpentier et al. |
| 6,569,200 B2 | 5/2003 | Wolfinbarger, Jr. et al. |
| 6,582,464 B2 | 6/2003 | Gabbay |
| 6,586,006 B2 | 7/2003 | Roser et al. |
| 6,586,573 B1 | 7/2003 | Besman et al. |
| 6,589,591 B1 | 7/2003 | Mansouri et al. |
| 6,605,667 B1 | 8/2003 | Badejo et al. |
| 6,613,278 B1 | 9/2003 | Mills et al. |
| 6,617,142 B2 | 9/2003 | Keogh et al. |
| 6,630,001 B2 | 10/2003 | Duran et al. |
| 6,652,594 B2 | 11/2003 | Francis et al. |
| 6,653,062 B1 | 11/2003 | DePablo et al. |
| 6,660,265 B1 | 12/2003 | Chen et al. |
| 6,685,940 B2 | 2/2004 | Andya et al. |
| 6,696,074 B2 | 2/2004 | Dai et al. |
| 6,734,018 B2 | 5/2004 | Wolfinbarger, Jr. et al. |
| 6,753,181 B2 | 6/2004 | Atala |
| 6,790,229 B1 | 9/2004 | Berreklouw |

(56) References Cited

U.S. PATENT DOCUMENTS

| | | |
|---|---|---|
| 6,797,000 B2 | 9/2004 | Simpson et al. |
| 6,828,310 B2 | 12/2004 | Barresi et al. |
| 6,861,211 B2 | 3/2005 | Levy et al. |
| 6,878,168 B2 | 4/2005 | Carpentier et al. |
| 6,893,666 B2 | 5/2005 | Spievack |
| 6,908,591 B2 | 6/2005 | MacPhee et al. |
| 6,919,172 B2 | 7/2005 | DePablo et al. |
| 6,933,326 B1 | 8/2005 | Griffey et al. |
| 7,008,763 B2 | 3/2006 | Cheung |
| 7,053,051 B2 * | 5/2006 | Hendriks et al. .............. 530/350 |
| 7,063,726 B2 | 6/2006 | Crouch et al. |
| 7,078,163 B2 | 7/2006 | Torrianni |
| 7,087,723 B2 | 8/2006 | Besman et al. |
| 7,214,344 B2 | 5/2007 | Carpentier et al. |
| 7,318,998 B2 | 1/2008 | Goldstein et al. |
| 7,338,757 B2 | 3/2008 | Wolfinbarger, Jr. et al. |
| 7,354,749 B2 | 4/2008 | Fisher et al. |
| 7,358,284 B2 | 4/2008 | Griffey et al. |
| 7,479,164 B2 | 1/2009 | Girardot et al. |
| 7,579,381 B2 * | 8/2009 | Dove ............................ 514/693 |
| 7,594,974 B2 | 9/2009 | Cali et al. |
| 7,648,676 B2 | 1/2010 | Mills et al. |
| 7,918,899 B2 * | 4/2011 | Girardot et al. ................ 8/94.11 |
| 2001/0000804 A1 | 5/2001 | Goldstein et al. |
| 2001/0004715 A1 | 6/2001 | Duran et al. |
| 2001/0020191 A1 | 9/2001 | Williams et al. |
| 2001/0023372 A1 | 9/2001 | Chen et al. |
| 2001/0025196 A1 | 9/2001 | Chinn et al. |
| 2001/0032024 A1 | 10/2001 | Cunanan et al. |
| 2001/0039459 A1 | 11/2001 | Stone |
| 2002/0001834 A1 | 1/2002 | Keogh et al. |
| 2002/0111532 A1 | 8/2002 | Pathak et al. |
| 2003/0035843 A1 | 2/2003 | Livesey et al. |
| 2003/0125805 A1 | 7/2003 | Johnson et al. |
| 2003/0135284 A1 | 7/2003 | Crouch et al. |
| 2003/0167089 A1 | 9/2003 | Lane |
| 2003/0217415 A1 | 11/2003 | Crouch et al. |
| 2004/0030381 A1 | 2/2004 | Shu |
| 2004/0086543 A1 | 5/2004 | Keogh et al. |
| 2004/0158320 A1 | 8/2004 | Simionescu et al. |
| 2004/0193259 A1 | 9/2004 | Gabbay |
| 2005/0079200 A1 | 4/2005 | Rathenow et al. |
| 2005/0119736 A1 | 6/2005 | Zilla et al. |
| 2005/0136510 A1 | 6/2005 | Hendriks et al. |
| 2006/0099326 A1 | 5/2006 | Keogh et al. |
| 2006/0110370 A1 | 5/2006 | Pathak et al. |
| 2006/0159641 A1 | 7/2006 | Girardot et al. |
| 2006/0177426 A1 | 8/2006 | Gibson et al. |
| 2006/0210960 A1 | 9/2006 | Livesey et al. |
| 2006/0217804 A1 | 9/2006 | Dove |
| 2006/0217805 A1 | 9/2006 | Dove |
| 2007/0050014 A1 | 3/2007 | Johnson |
| 2007/0292459 A1 | 12/2007 | Cooper et al. |
| 2008/0302372 A1 | 12/2008 | Davidson et al. |
| 2008/0319166 A1 | 12/2008 | Shen |
| 2009/0041729 A1 | 2/2009 | Wolfinbarger, Jr. et al. |
| 2009/0164005 A1 | 6/2009 | Dove et al. |

FOREIGN PATENT DOCUMENTS

| | | |
|---|---|---|
| WO | 96/13227 A1 | 5/1996 |
| WO | 98/43556 A1 | 10/1998 |
| WO | 00/32252 A1 | 6/2000 |
| WO | 01/41828 A1 | 6/2001 |
| WO | 03/037227 A2 | 5/2003 |
| WO | 2004/082536 A1 | 9/2004 |
| WO | 2006/099334 A2 | 9/2006 |
| WO | 2008073582 A2 | 6/2008 |

OTHER PUBLICATIONS

Zilla et al., Diamine-extended Glutaraldehyde and Carbodiimide Crosslinks act syngerstically in mitigating bioprosthetic aortic wall calcification, The Journal of Heart Valve Disease, 14:538-545.*

Zilla'ATS, Zilla et al., Carbodiimide Treatment Dramatically Potentiates the Anticalcific Effect of Alpha-Amino Oleic Acid on Glutaraldehyde-Fixed Aortic Wall Tissue, Ann. Thorac. Surg. 79:905-10.*

International Search Report for corresponding international patent application No. PCT/US2011/060980 dated Jul. 9, 2012.

Estler, C.-J. et al., "Lehrbuch der allgemeinen und systematischen Pharmakologie und Toxikologie," Schattauer, 1986.

Hof, Herbert et al., "Duale Reihe/Medizinische Mikrobiologie," George Thieme Verlag, 2000, Ed. 3.

Gilbert, Thomas W. et al., "Decellularization of tissues and organs," Biomaterials, vol. 7, Mar. 7, 2006.

Glycerin, http://de.wikipedia.org/wiki/Glycerin.

Carpentier, A., et al., "Biological Factors Affecting Long-Term Results of Valvular Heterografts," Forty-ninth Meeting of the American Association for Thoracic Surgery, San Francisco, CA, Mar. 31-Apr. 2, 1969.

Chanda, J., et al., "Heparin in Calcification Prevention of Porcine Pericardial Bioprostheses," Biomaterials, Elsevier Science Publishers, vol. 18, No. 16, ISSN: 0142-9612, Aug. 1, 1997.

Dahm, Manfred, et al., "Effects of Surface Seeding with Vital Cells on the Calcium Uptake of Biological Materials for Heart Valve Replacement," J Heart Valve Dis, vol. 5, No. 2, Mar. 1996, 148-151.

Jayakrishnan, A., et al., "Glutaraldehyde as a Fixative in Bioprostheses and Drug Delivery Matrices," Biomaterials, vol. 17, Issue 5, 1996, pp. 471-484.

Khora, Eugene, "Methods for the Treatment of Collagenous Tissues for Bioprostheses," Biomaterials, vol. 18, Issue 2, Jan. 1997, pp. 95-105.

R Parker, et al. Storage of Heart Valve Allografts in Glycerol With Subsequent Antibiotic Sterilisation, Thorax, 1978, 638-645, vol. 33:5, British Thoracic Society, London, UK.

Zilla, P., et al., "Carbodiimide Treatment Dramatically Potentiates the Anticalcific Effect of Alpha-Amino Oleic Acid on Glutaraldehyde-Fixed Aortic Wall Tissue," The Annals of Thoracic Surgery, Elsevier, vol. 79, No. 3, ISSN: 0003-4975; Mar. 1, 2005.

* cited by examiner

DOUBLE CROSS-LINKAGE PROCESS TO ENHANCE POST-IMPLANTATION BIOPROSTHETIC TISSUE DURABILITY

RELATED APPLICATION DATA

The present application claims priority under 35 U.S.C. §119(e) to U.S. Provisional Application No. 61/414,726 filed Nov. 17, 2010.

FIELD OF THE INVENTION

The present invention provides methods for making bioprosthetic devices from collagen-containing tissue. More particularly, a double cross-linkage process to enhance post-implantation bioprosthetic tissue durability is described.

BACKGROUND OF THE INVENTION

In 1968, Alain Carpentier first introduced the use of glutaraldehyde ("Glut") to treat animal tissues before implantation, leading to the first implantation of a valvular bioprosthesis in man. Carpentier, A. et al., *J Thorac Cardiovasc Surg.* 1969 October; 58 (4): 467-83. In the following years the process was improved, and the valve was mounted into a stent leading to the concept of a bioprosthesis. Carpentier, *A. Med Instrum.* 1977; 11 (2): 98-101.

As experience grew several limitations became apparent, including tissue calcification and collagen degeneration. Calcium mitigation was obtained by adding a surfactant and ethanol to the glutaraldehyde process. Carpentier A., Nashef A. et al. *Circulation* 70 (3Pt2): 1165-68; and intensively described in U.S. Pat. No. 4,885,005 Improved glutaraldehyde fixation was obtained by immersing the tissue in a heated glutaraldehyde solution, preferably at a temperature of about 45 to 55° C. for a period of time ranging from 10 to 12 days, according to the method first proposed by Carpentier S. et al., *Ann. Thorac. Surg.* Dec. 66 (6 Suppl.) 3264-6, which is incorporated herein in its entirety.

Although these techniques have proven to be efficient in reducing tissue calcification and enhancing tissue stability, there remains a need for further improvements, in particular to enlarge the use of valvular bioprosthesis in young patients.

Diamines, including lysine or Jeffamine, have been proposed by others to crosslink free aldehyde groups in bioprosthetic tissues. Jeffamine®, sold by Huntsman International, was first used by Hendricks et al (U.S. Pat. No. 6,166,184 and U.S. Pat. No. 7,053,051) to avoid treating the tissue with glutaraldehyde, which was said to enhance calcification. The drawbacks in these methods are that amino groups from adjacent collagen molecules and residual amino groups from the diamines were not crosslinked or further modified. As a result, tissue stability was compromised. Thus, there remains a need for improved bioprosthetic tissue with enhanced post-implantation durability.

SUMMARY OF THE INVENTION

The present invention teaches an improved tissue treatment process which comprises the novel combination of: 1) a heated glutaraldehyde solution at a higher concentration or for an increased time of fixation to durably crosslink free amino groups, and 2) a diamine treatment, to durably crosslink free aldehyde groups.

One aspect of the present invention is a method for preparing bioprosthetic implant tissue, comprising fixing bioprosthetic implant tissue by treatment with glutaraldehyde at 0.1 to 10 wt % concentration and at elevated temperature, capping said fixed tissue by treatment with a diamine crosslinking agent, and treating said capped tissue with about 0.6 wt. % glutaraldehyde. The fixing step is conducted at about 50° C. and pH 5.8 for 2 to 25 days, and the capping step is preferably conducted in the presence of a reducing agent, such as sodium borohydride. The diamine crosslinking agent can be Jeffamine, Jeffamine D, lysine, a multifunctional polymer, or an organic solvent, and can be delivered in water or a buffer solution.

In one embodiment, the diamine crosslinking agent is Jeffamine at a concentration of 0.01M to 1M, and the capping treatment is done for a period of 1 hour to 7 days at temperatures between 4° and 50° C. at pH between 8 and 13. Preferably, the concentration is 0.1M and the treatment is done for 48 hours at 37° C. and pH 11.7.

In one embodiment, the sodium borohydride is used as an adjunct to Jeffamine at a concentration between 0.05% and 1%, for a period of 1 hr to 3 days, at a temperature between 4° and 40°. Preferably, the concentration is 0.25% and the treatment is done for 24 hours at 37° C.

In one embodiment of the method, during the fixing step, the glutaraldehyde concentration is 0.6 to 10 wt. %, and the treatment is carried out to for 1 to 90 days, at a temperature from 37 to 75° C., at a pH of 5.4 to 6.8. Preferably, the glutaraldehyde concentration is 5%, and the treatment is carried out for a time of 18 days, at a temperature of 52±2.5° C., at a pH of 5.8. Alternatively, the heat treatment is achieved in a non-Glut solution.

In yet another embodiment, the fixed tissue is treated in a surfactant solution thereby substantially eliminating phospholipids. The surfactant solution contains formaldehyde, ethanol and Tween 80.

The tissue being treated can be a heart valve or valve leaflets retrieved from animals, mounted within a stent and used as a treated whole valve. It can be a native valve treated and mounted as a whole valve, and the treated whole valve is stored in a glutaraldehyde solution of 0.1% to 0.6 wt. % concentration, preferably the glutaraldehyde storage solution has a concentration of 0.6%. Alternatively, the treated whole valve can be stored as a dehydrated valve, wherein tissue dehydration is achieved in a glycerol solution. The dehydrated valve can be sterilized in ethylene oxide.

Another aspect of the present invention is a bioprosthetic implant tissue made by a process comprising fixing bioprosthetic implant tissue by treatment with 0.1 to 10 wt. % glutaraldehyde, at elevated temperature; capping said fixed tissue by treatment with a diamine crosslinking agent; and treating said capped tissue with about 0.6 wt. % glutaraldehyde.

Another aspect of the present invention is a method of preparing bioprosthetic implant tissue comprising:
 a) treating bioprosthetic implant tissue with at least 0.2 wt. % glutaraldehyde at pH 5-6.8 between 45°-75° C. for 1 to 90 days;
 b) capping said tissue by treatment with a diamine crosslinking agent followed by reduction of Schiff base with $NaBH_4$,
 c) treating said capped tissue with about 0.6 wt. % glutaraldehyde at room temperature, preferably for at least 1 month;
 d) treating the tissue with surfactant in an alcohol solution with formaldehyde (FET); and
 e) storing the tissue in 0.6% glutaraldehyde at 4° C.;
 wherein steps a), b), c) and d) are performed while stirring.

BRIEF DESCRIPTION OF THE FIGURES

Experiments were carried out using subcutaneous implantation in rats of treated tissue specimen.

DETAILED DESCRIPTION OF THE INVENTION

Heart valve replacement may be indicated for native valve stenosis and when the native valve leaks or regurgitates, such as when the leaflets are calcified. The native valve may be excised and replaced with either a biological or mechanical valve prosthesis.

Bioprosthetic valves have biological tissue leaflets supported by a base structure that are implanted into the blood stream. As examples, biological leaflets mounted within a support structure are used in the CARPENTIER-EDWARDS® Porcine Heart Valve and in the CARPENTIER-EDWARDS® PERIMOUNT® Pericardial Heart Valve, available from Edwards Lifesciences of Irvine, Calif. Although these valves have been associated with excellent long term function in human, some of them have shown evidence of calcification, particularly in young patients.

The present invention provides an improved bioprosthetic tissue treatment process that greatly reduces the potential for calcification after implantation of glutaraldehyde-treated tissue by using a combination of crosslinking free amino groups, using high temperature, high concentration Glut and crosslinking free aldehyde groups by diamines.

A preferred embodiment uses JEFFAMINE polyetheramines, which are an expanding family of Huntsman products that contain primary amino groups attached to the end of a polyether backbone. The polyether backbone is normally based on either propylene oxide (PO), ethylene oxide (EO), or mixed PO/EO. Thus they are called "polyetheramines." The JEFFAMINE polyetheramine family comprises monoamines, diamines, and triamines based on this core structure. Recently, the addition of secondary, hindered, high-conversion, and polytetramethylene glycol (PTMEG) based polyetheramines have become available.

"Bioprosthetic tissue" includes, without limitation, bovine pericardium and porcine tissue which are commonly used in bioprosthetic heart valves, blood vessels, skin, dura mater, pericardium, small intestinal submucosa ("SIS tissue"), tissue heart valves, ligaments and tendons. In one embodiment, the tissue comprises pre-cut heart valve leaflets mounted and treated in a suitable apparatus. Alternatively, the tissue may be bulk sheets of tissue treated in a suitable apparatus.

"Implants" in the present application refer not only to heart valves, including transcatheter heart valves, but also to vascular prostheses and grafts, tissue grafts, bone grafts, and orbital implant wraps, among others.

A "bioprosthetic heart valve" refers to a fully assembled prosthetic valve made at least partly from bioprosthetic tissue. Some whole porcine valves are used in so-called "stentless" bioprosthetic valves in which there is very little, if any, synthetic material added for support or anchoring purposes.

A "stented" bioprosthetic valve typically has some kind of synthetic (e.g., polymer or metallic) support for the leaflets, which may be the leaflets of a whole porcine valve or separate bovine pericardial leaflets. Heart valves contemplated herein include surgical heart valves, transapical heart valves, transfemoral heart valves and other types of heart valves.

Implantable biological tissues of the invention can be formed of human tissues preserved by freezing (i.e., cryopreservation) of homograft tissues, or tissues from animal preserved by chemical fixing (i.e., bioprosthetic tissues). These tissues contain connective proteins (i.e., collagen and elastin) which act as the supporting framework.

Chemical fixation of biological tissues involves exposing them to one or more chemical fixatives (i.e., tanning agents) which form crosslinks between the polypeptide chains within a given collagen molecule (i.e., intramolecular cross-linkages), or between adjacent collagen molecules (i.e., intermolecular cross-linkages). Examples of chemical fixatives that have been used to crosslink collagenous tissues include: formaldehyde, glutaraldehyde, dialdehyde starch, hexamethylene diisocyanate and certain polyepoxy compounds.

An ongoing problem with bioprosthetic materials is that the connective tissue proteins, collagen and elastin, can become calcified after long term implantation in the body particularly in young patients. Calcification produces undesirable stiffening or degradation of the bioprosthesis, which may lead to valve failure.

Glutaraldehyde (or "Glut") has been the most widely used fixative since the discovery of its anti-immunological and anti-degenerative effects. Carpentier, A. et al., *J Thorac Cardiovasc Surg.* 1969 October; 58 (4): 467-83. However, glutaraldehyde treatment does not prevent calcification of the tissue's potential calcium binding sites on collagen, elastin, ground substance and lipids, which can lead to calcification in vivo. This propensity for calcification can be reduced by applying various chemical treatments as described in U.S. Pat. No. 4,729,139 (Nashef); U.S. Pat. No. 4,885,005 (Nashef et al.); U.S. Pat. No. 4,648,881 (Carpentier et al.); U.S. Pat. No. 5,002,566 (Carpentier); EP Patent No. 103947 (Pollock et al.), U.S. Pat. No. 5,476,516 (Seifter et al.), U.S. Pat. No. 5,215,541 (Nashef et al.) and U.S. Pat. No. 5,862,806 (Cheung).

U.S. Pat. No. 6,471,723 (Ashworth et al.) and U.S. Pat. No. 4,786,287 (Nashef et al.) describe calcification mitigation by addition of a variety of amines to the aldehyde groups in glutaraldehyde-fixed tissue. U.S. Pat. No. 5,476,516 (Seifter, et al.) teaches the addition of polyols (e.g., glycerol) and alcohols to bioprosthetic tissues as a calcification mitigation treatment. U.S. Pat. No. 6,509,145 (Torrianni) and U.S. Pat. No. 7,078,163 (Torrianni) address oxidation of bioprosthetic tissue for calcification mitigation. U.S. Pat. No. 6,630,001 (Duran, et al.) and U.S. Pat. No. 6,277,555 (Duran, et al.) discuss the use of glycerol preservation first proposed by Zerbini and lyophilization of tissue. U.S. Pat. No. 6,352,708 (Duran, et al.) includes glycerol preservation of fresh, "non-fixed" tissue, and treatments with glycerol and heparin.

A method of calcium mitigation by elevated-temperature fixation of the tissue in glutaraldehyde was described in U.S. Pat. No. 6,561,970 (Carpentier et al.), and in combination with relative tissue/fluid movement in U.S. Pat. No. 5,931,969 (Carpentier et al.). A technique involving adjusting the pH of a glutaraldehyde fixation solution is disclosed in U.S. Pat. No. 6,878,168 (Carpentier et al.).

Described herein is a method of treating bioprosthetic implant tissue to reduce in vivo calcification, comprising: fixing bioprosthetic implant tissue with high temperature and high concentration glutaraldehyde, and then treating the fixed tissue with a diamine crosslinking solution to mitigate calcification.

Tissue treatment with glutaraldehyde, Tween (polyoxyethylene 20 sorbitan monooleate), ethanol, and optionally with formaldehyde, can provide useful fixation of the tissue. However, these compounds will also generate new binding sites capable of interacting with or attracting calcium. Tissues treated with glutaraldehyde contain free aldehyde groups which cause increased toxicity, and higher calcification.

Thus, described herein is a method to cap these newly formed binding sites prior to implantation into the body. The term "capping" refers to the blocking, removal, or alteration of a functional group that would have an adverse effect on the bioprosthesis properties.

Unlike prior art tissue processes in which the separate goals are merely to fix the tissue with glutaraldehyde at low concentration, or to cap tissue amines with a blocking agent, the present method combines the two processes, i.e., cross-linking free aldehyde groups with a diamine and free amino groups with a high concentration dialdehyde, while at the same time capping free aldehyde groups, preferably under reducing conditions.

In a preferred embodiment, the glutaraldehyde fixation step is carried out before capping the dialdehyde groups with diamines, preferably using heated Glut at 50° C. for 3 to 25 days. The Glut fixation is followed by treatment with a Jeffamine diamine under reducing conditions (e.g., sodium borohydride) in order to cap the aldehyde groups in fixed tissue, and further cross-link proteins in the tissue, thereby enhancing its stability in vivo.

The present fixing/capping/crosslinking process preferably includes chemical reduction of the tissue, which, when applied in the presence of a polymeric diamine, will permanently connect the crosslinking agent to the target aldehyde groups.

For example, the addition of a Jeffamine, such as Jeffamine D, to the tissue will simultaneously cap and crosslink the aldehyde groups, while a reducing agent (e.g., sodium borohydride) will reduce any Schiff base created by reaction of the aldehyde with the amine groups. Thus aldehyde groups are ultimately replaced by bridging groups or polymeric amine moieties, which may be beneficial for tissue hydration, flexibility, and cell interactions.

Other diamine capping/crosslinking agents can be used instead of Jeffamine, such as lysine or polymeric molecules. Reducing agents usable in aqueous solution other than sodium borohydride are known by those skilled in the art and are included in the scope of this invention, including potassium borohydride, cyanoborohydride and others.

Glutaraldehyde Treatment

Glutaraldehyde treatment comprises 3 steps: First, fixation of the tissue in 0.6% Glut at pH 7.4 at room temperature for at least 1 month with stirring (Glut Fixation I 10, FIG. 7); then further fixation in heated Glut at 45-75° C. for 1 to 90 days with stirring (Heat Treatment 12, FIG. 7); then further fixation in 0.6% at room temperature for at least 1 month (Glut Fixation II 14, FIG. 7).

Jeffamine Crosslinking and Reduction by Sodium Borohydride

The glutaraldehyde-fixed tissue is rinsed in PBS buffer solution to remove any excess glutaraldehyde adhering to the tissue. The tissue is then exposed first to a capping/crosslinking solution of Jeffamine diamines in distilled water (DW) at a concentration of 0.1±0.01M under agitation for 24 hours at 37° C. and secondly in Jeffamine and 0.25% sodium borohydride solution at 37° C. for another 24 hours under agitation (Capping 16, FIG. 7). The tissue is removed from the solution and rinsed during a few minutes at room temperature in 0.9% NaCl solution.

Surfactant Treatment

The tissue is then treated in a surfactant solution containing formaldehyde, ethanol and Tween 80 for 9 hours at 32° C. (Surfactant 18, FIG. 7). After rinsing three times in 0.9% NaCl solution, storage is carried out either in Glut or in glycerol according to the following process.

Storage

1—Storage in 0.6% Glut at 4° C. Sterilization is achieved by the Glut solution (Storage in Glut 20, FIG. 7)

2—Storage in Glycerol (optional). After the tissue has been processed through a standard final bioburden reduction step and then through 0.6% Glut step for at least 1 month, it may undergo a glycerol treatment in a solution of 75 wt % glycerol and 25 wt. % ethanol. The tissue is soaked in this solution for one hour at room temperature. During this time most of the water molecules present in the pericardial tissue are replaced with glycerol. The tissue is removed from the solution and placed in a clean hood to allow any excess solution to evaporate or drip off the tissue (Dry Storage 22, FIG. 7).

Sterilization

Sterilization is achieved by ethylene oxide (EO). The dehydrated tissue is packaged in double sterile barrier packaging consisting of a rigid tray (PETG) with a Tyvek lid. The package should be sealed in a cleanroom, and can be sterilized in 100% ethylene oxide.

In embodiments where the fixed and crosslinked tissue is dehydrated, such as in an ethanol/glycerol solution, the glycerol may include an antioxidant and may contain a water-soluble wax. The tissue is then allowed to dry and then subjected to final sterilization (e.g., ethylene oxide, gamma irradiation, or electron beam irradiation).

The calcification mitigant preferably contains a capping/crosslinking agent selected from:
 polymeric diamines, such as Jeffamine D, ED and EDR,
 diamino acids, such as lysine,
 hydrophilic multifunctional polymers containing at least two amino groups,
 hydrophobic multifunctional polymers containing at least two amino groups.

The reducing agent may be sodium borohydride, potassium borohydride, cyanobrohydride and the like.

The chemical anti-oxidant is desirably selected from a water soluble antioxidant such as ascorbic acid, a fat soluble antioxidant such as tocopherols, a carbohydrate such as fructose, sucrose, or mannitol a hindered phenol such as butylated hydroxytoluene (BHT), a hindered amine light stabilizer (HALS) such as p-phenylamine diamine, trimethyl dihydrodquinoline, or alkylated diphenyl amines a phosphite/phosphonite such as triphenyl phosphine, and a thioester such as a thiocinnamate.

The diamine is desirably delivered in one or a combination of the following solutions:
- an aqueous solution such as an aqueous buffered solution, water, short chain alcohols, glycerol, or plasticizers,
- an organic solvent, and
- an organic buffered solution.

The diamine crosslinking agents are generally used a) at a concentration of 0.02M to 1M, preferably 0.1M; b) for a period of 1 hour to 4 days, preferably 48 hours; c) at temperatures between 4° and 50° C., preferably 37° C.; and d) at pH between 8 and 13, preferably 11.7.

The reducing agents, such as sodium borohydride, are generally used a) at a concentration between 0.05% and 1%, preferably 0.25%; b) for a period of 1 hr to 3 days, preferably 24 hr; c) at temperature between 4° and 40°, preferably 37° C.

During the high temperature fixing step, the glutaraldehyde concentration is generally 0.1 to 6 wt. %, preferably 0.6 wt. %; and treated for 1 to 25 days, preferably 18 days at a temperature from 20 to 70° C., preferably 52° C.+/−2.5° C.; at a pH between 5.4 to 6.8, preferably 5.8. The other fixing steps preceding or following the high temperature step are generally 0.6% Glut at pH 7.4 at room temperature. In another embodiment, heated Glut can be replaced by heated buffer solution under similar conditions.

In a preferred embodiment the fixed tissue is treated in a surfactant solution to eliminate phospholipids. For example the surfactant solution may contain formaldehyde, ethanol and Tween 80.

In one embodiment of the invention the prosthetic tissue is a heart valve or leaflets retrieved from animals, mounted within a stent and used as a treated whole valve. In another embodiment, the tissue is bovine pericardial tissue used to form heart valve leaflets which are used to produce a bioprosthetic heart valve.

In another embodiment the processed tissue is a native valve treated and mounted as a whole valve. A treated whole valve may be stored in a glutaraldehyde solution at a concentration from 0.1% to 2%, preferably 0.6 wt. %.

In one embodiment the treated whole valve is stored as a dehydrated valve; preferably tissue dehydration is achieved in a glycerol solution. In a preferred embodiment the dehydrated valve is sterilized in ethylene oxide.

In one embodiment for preparing a bioprosthetic implant tissue, the glutaraldehyde fixing step is conducted at about 50° C. and pH 5.8 for at least 7 days, and capping with a diamine crosslinking agent is conducted in the presence of a reducing agent, preferably sodium borohydride.

To better understand the calcification properties of the invention, charts are presented in the figures which are based on subcutaneous testing of multiple samples.

Figure 1:
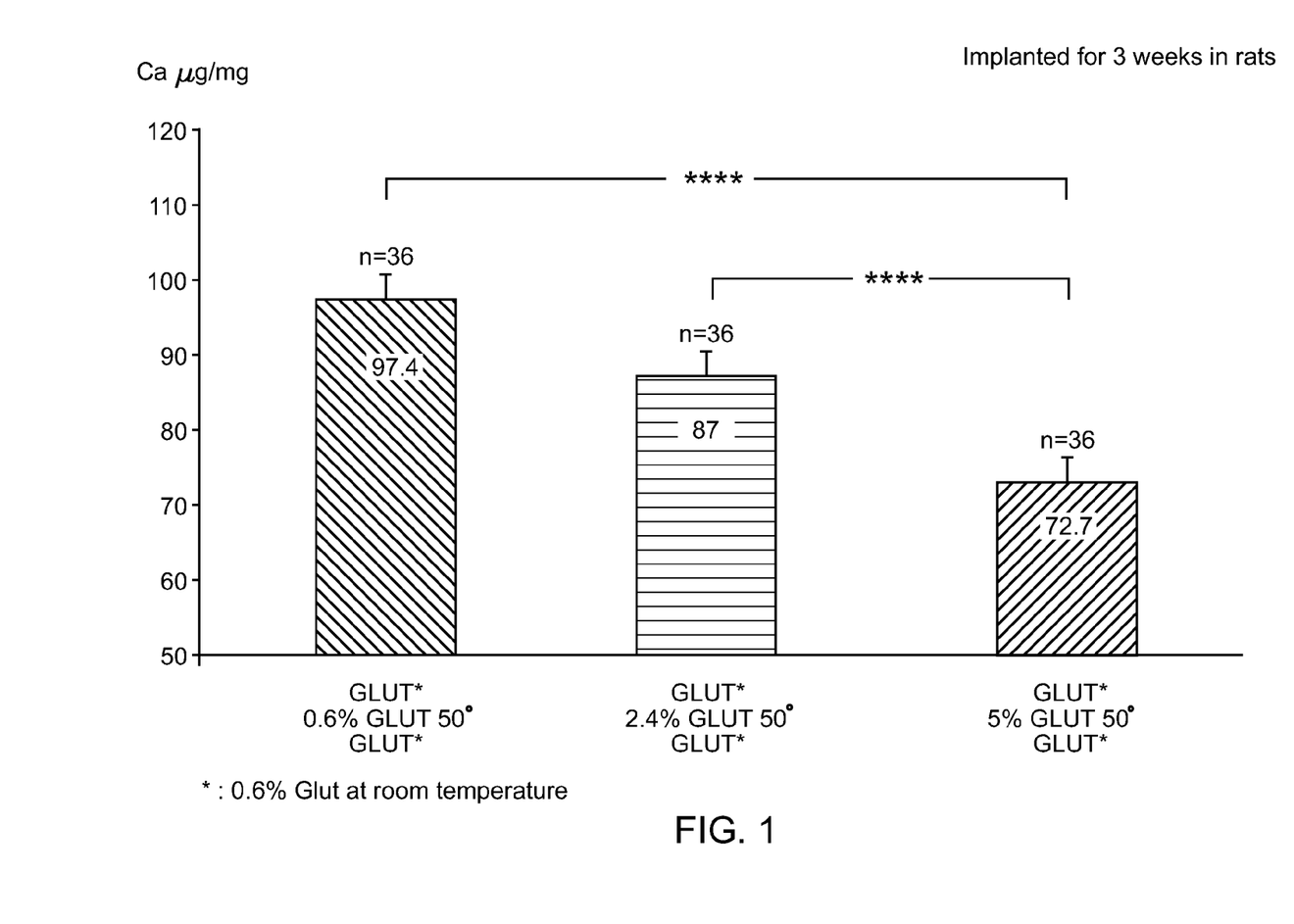
FIG. 1 is a chart showing the calcium mitigation effect of high temperature Glut at different Glut concentrations preceded by treatment of the tissue in 0.6% Glut at room temperature and followed by treatment of the tissue in 0.6% Glut at 4° C. Results show that, contrary to expectation, high concentration Glut at 50° C. provides more calcium mitigation than low concentration, provided that it is followed by a low concentration glut treatment.

FIG. 1 shows calcium mitigation effect of high temperature Glut at different Glut concentrations. Bovine pericardial tissue was first treated with 0.6% Glut at room temperature. Then the control group was treated with 0.6% Glut for 6 days at 50° under agitation. The two other groups were treated with 2.4% and 5% Glut for 6 days at 50° under agitation. Tissues were implanted for 3 weeks in rats. The results show that the calcium mitigation in the 5% Glut group is superior to the 2.4% and 0.6% Glut groups (97.40 v. 87.00 v. 72.70 μg/mg), a decrease of 25%.

Figure 2:
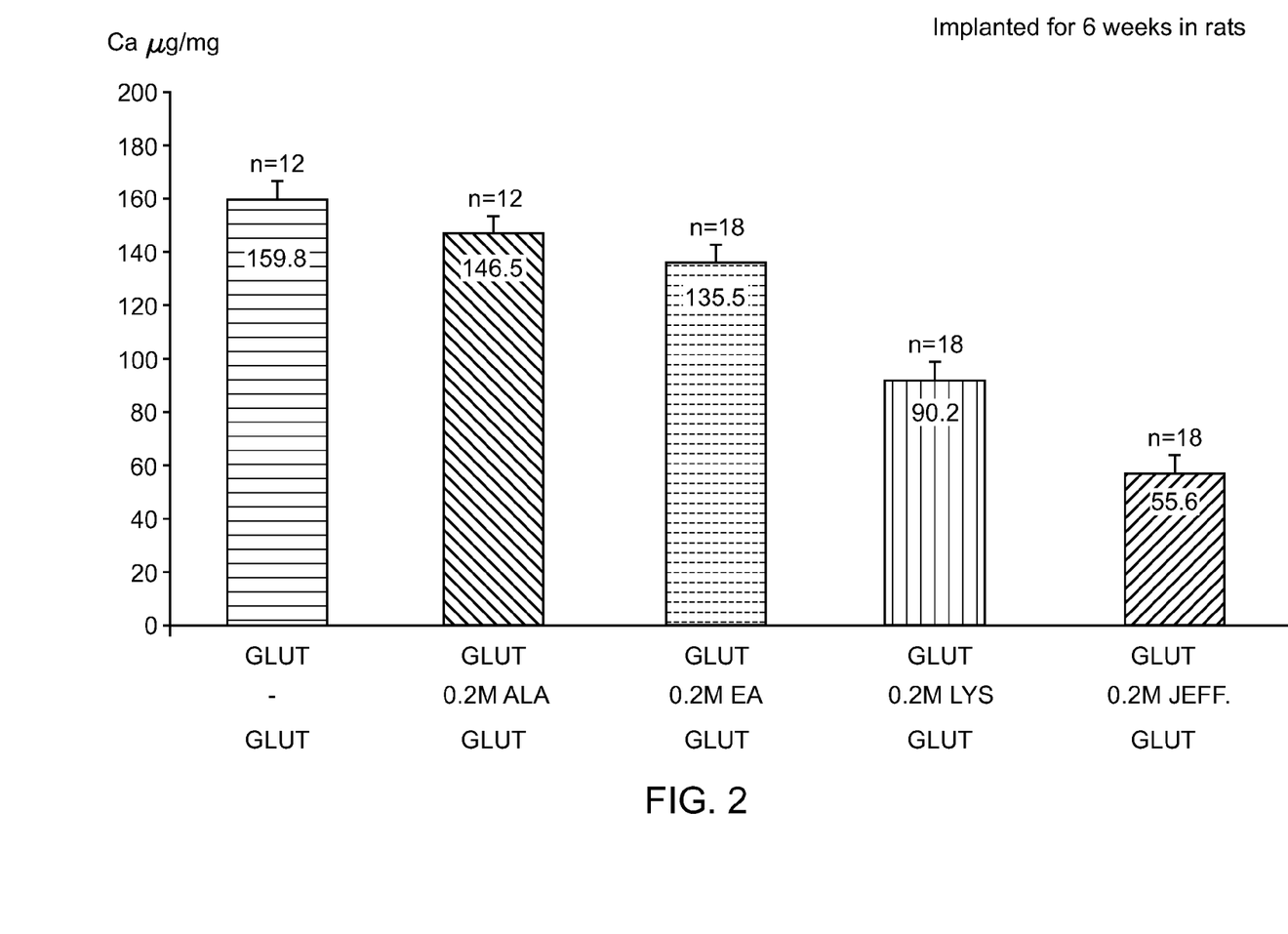
FIG. 2 is a chart comparing calcification of Glut treated tissue exposed to different amines: ALA: alanine; EA: ethanolamine, LYS: lysine, JEFF: Jeffamine.

FIG. 2 shows tissue calcification of pericardium specimen treated with different amines after implantation in rat for 6 weeks. The control samples were fixed with glutaraldehyde only. The test samples were fixed with glutaraldehyde and then capped with alanine (ALA), ethanolamine (EA), lysine (LYS) or Jeffamine (JEFF). The results show that the crosslinking agent Jeffamine (55.6 ug/mg) was superior to lysine (90.2 ug/mg); which may also be functioning as a crosslinker, and both were superior to the monoamino compounds ethanolamine (135.5 ug/ml) and alanine (146.5 ug/mg).

Figure 3:
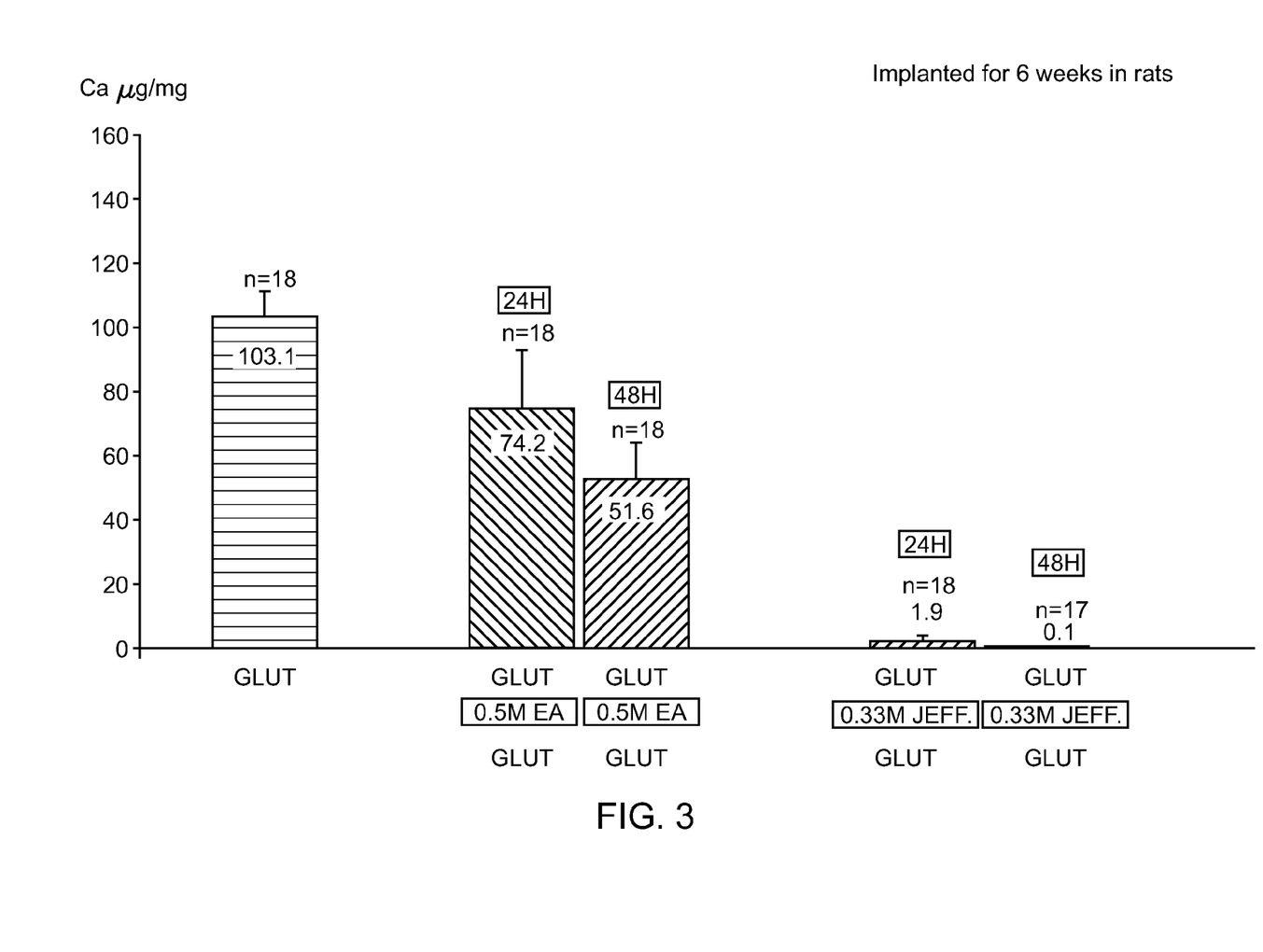
FIG. 3 is a chart showing the calcium mitigation effect of ethanolamine and Jeffamine with different durations of treatment.

FIG. 3 shows the calcification mitigation of glutaraldehyde-fixed tissue treated with 0.3M Jeffamine for 24 hours or 48 hours compared to that treated with 0.5M ethanolamine for the same time, then implanted subcutaneously in rats for 6 weeks. Results show that Jeffamine is superior to ethanolamine.

Figure 4:
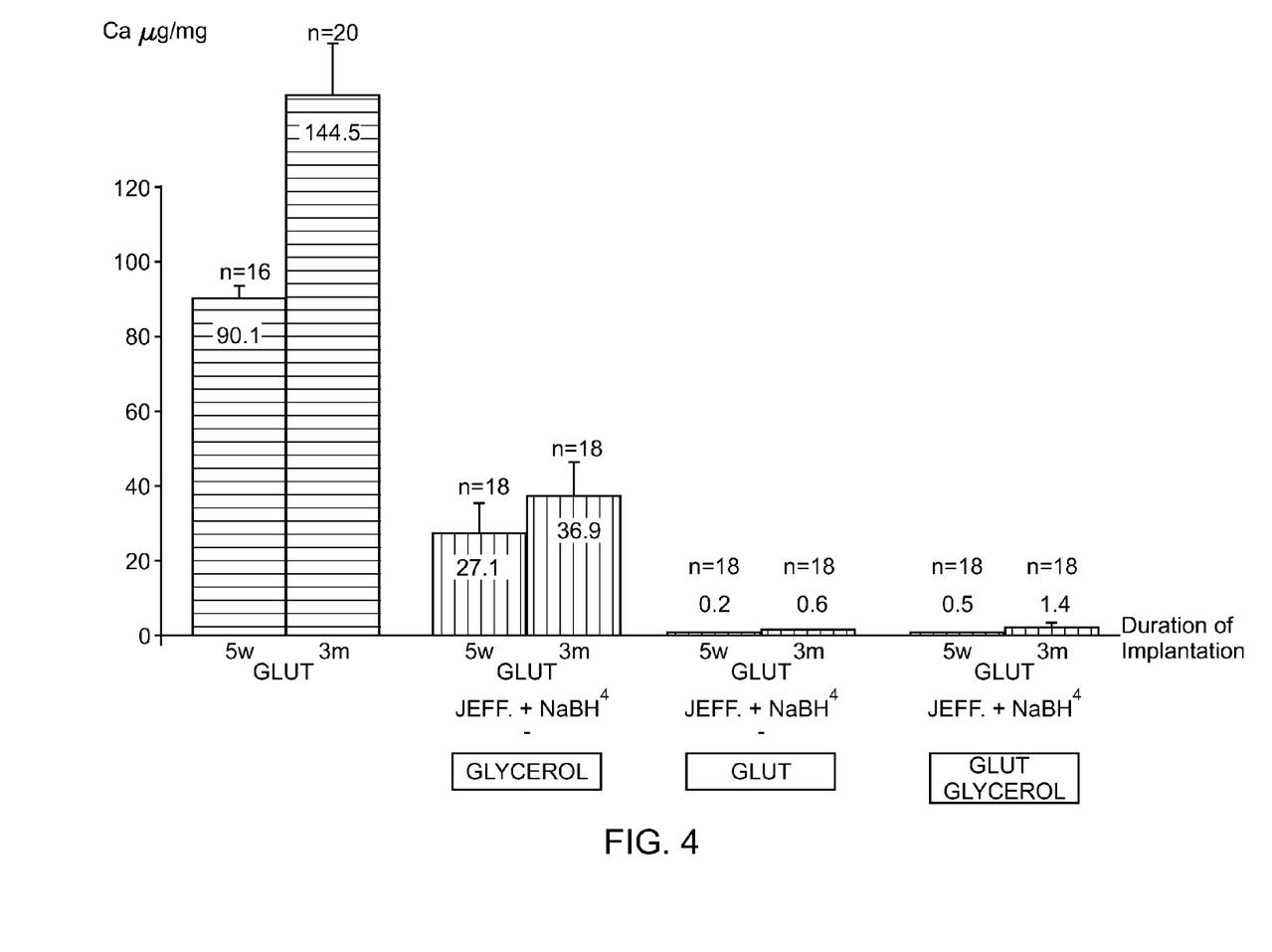
FIG. 4 is a chart showing calcium mitigation by Jeffamine treatment and Schiff base reduction by NaBH4 and followed by different storages: glycerol, Glut, Glut then glycerol

FIG. 4 shows the calcification resistance of glutaraldehyde-fixed tissue treated with Jeffamine and borohydride, then post-treated with glutaraldehyde. After implantation for 3 months in rats, a decrease of 99.6% calcium was observed (144.5 vs. 0.6 μg/mg) in Jeffamine and $NaBH_4$ treated tissue. Different conditions of storage: Glut or 75% glycerol/25% ethanol were analysed.

Figure 5:
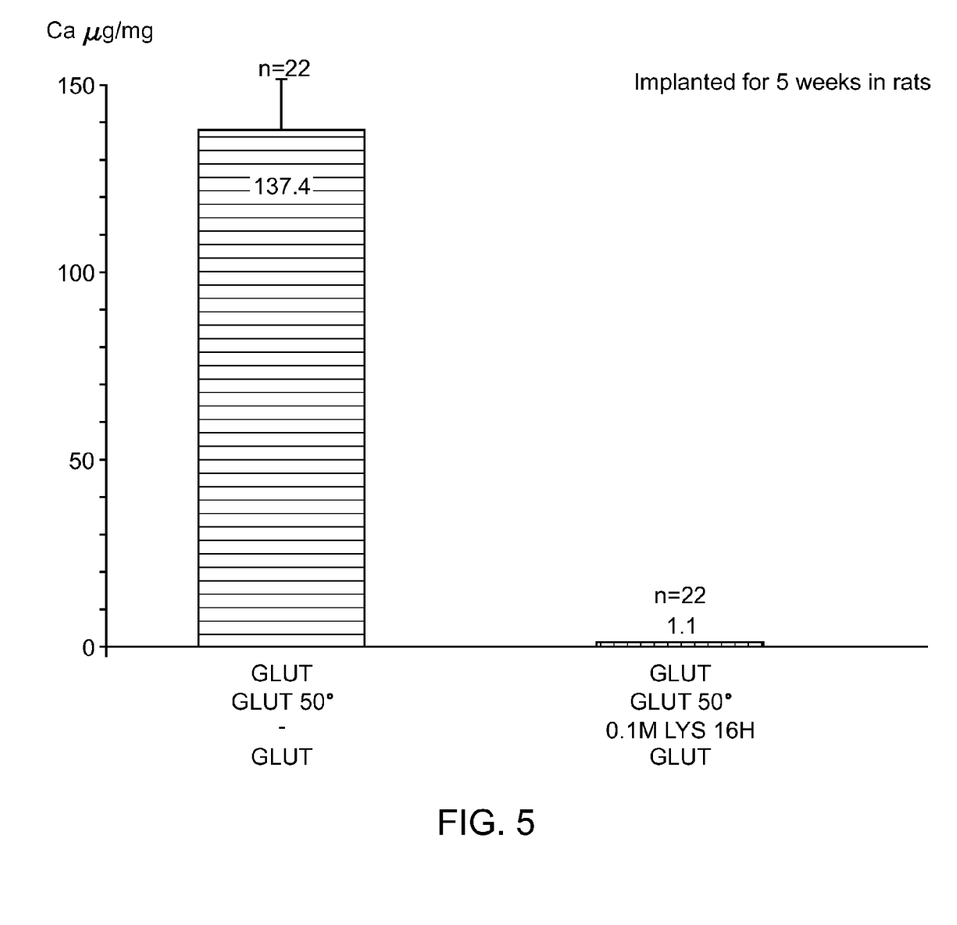
FIG. 5 is a chart showing calcium mitigation by double crosslinkage: Heated Glut followed by lysine.

FIG. 5 shows high calcium mitigation of Glut tissue treated by lysine for 16 hours preceded by heat Glut treatment. Compared to the control group without lysine, the group with lysine shows a 99.2% calcium decrease after implantation for 5 weeks in rats.

Figure 6:
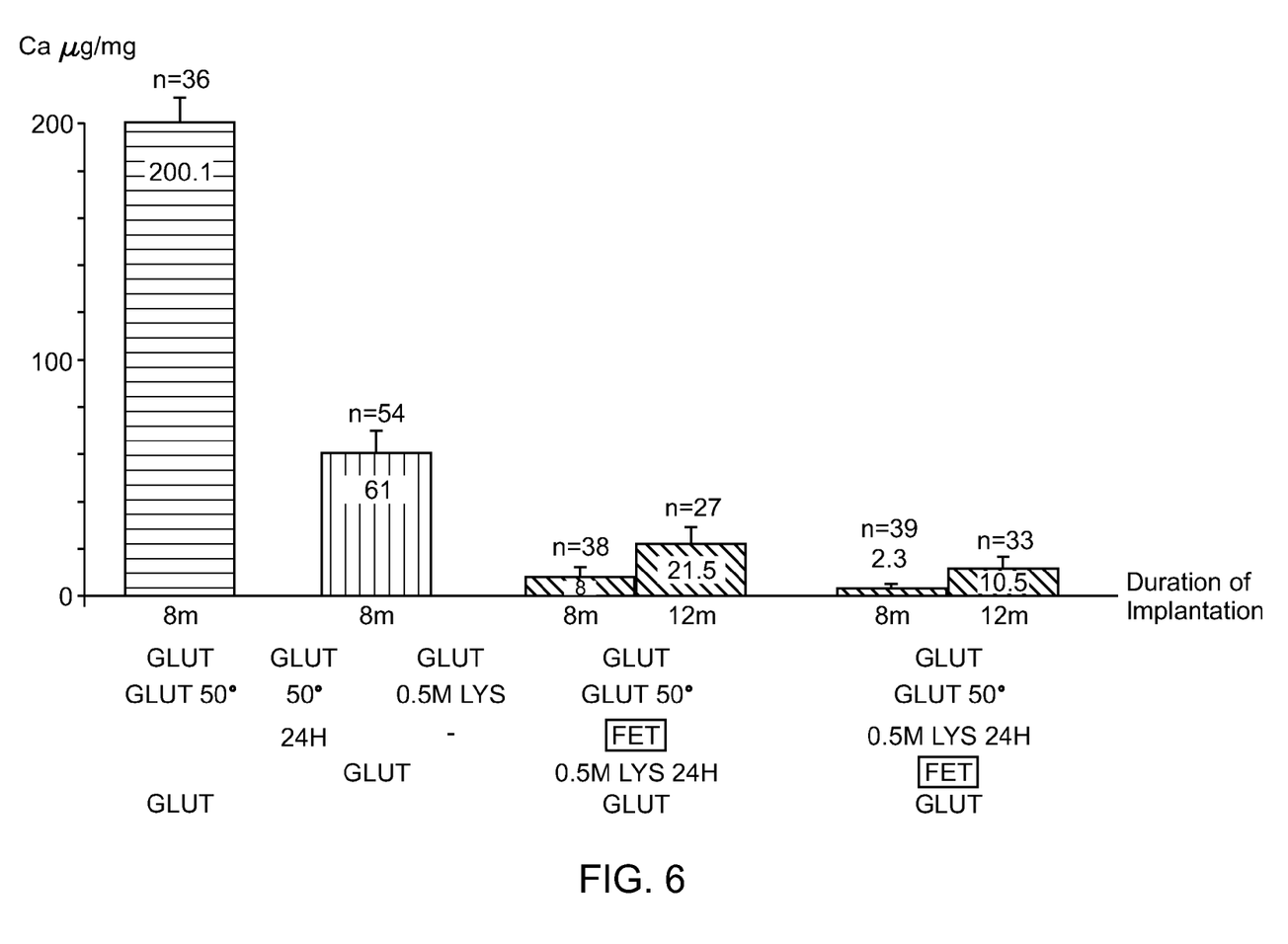
FIG. 6 is a chart showing the very long term—up to 12 months—effect of the double crosslinkage process, comprising high temperature Glut, diamine crosslinking and surfactant (FET).

FIG. 6 shows the calcium mitigation effect of a treatment comprising heated Glut, lysine and surfactant. First the tissue was exposed to a concentrated (5%) glutaraldehyde solution at pH 5.8 at 50° C. for 6 days under agitation, then to 0.6% Glut at room temperature for at least 3 days. Capping/crosslinking with 0.5M lysine in distilled water (DW) for 24 hours at 37° C., was followed by treatment with 0.6% Glut at pH 7.4 for 24 hrs. Surfactant treatment (FET) for 9 hrs at 32° was done either before or after lysine treatment. Storage is done in 0.6% Glut at 4° C.

Figure 7:
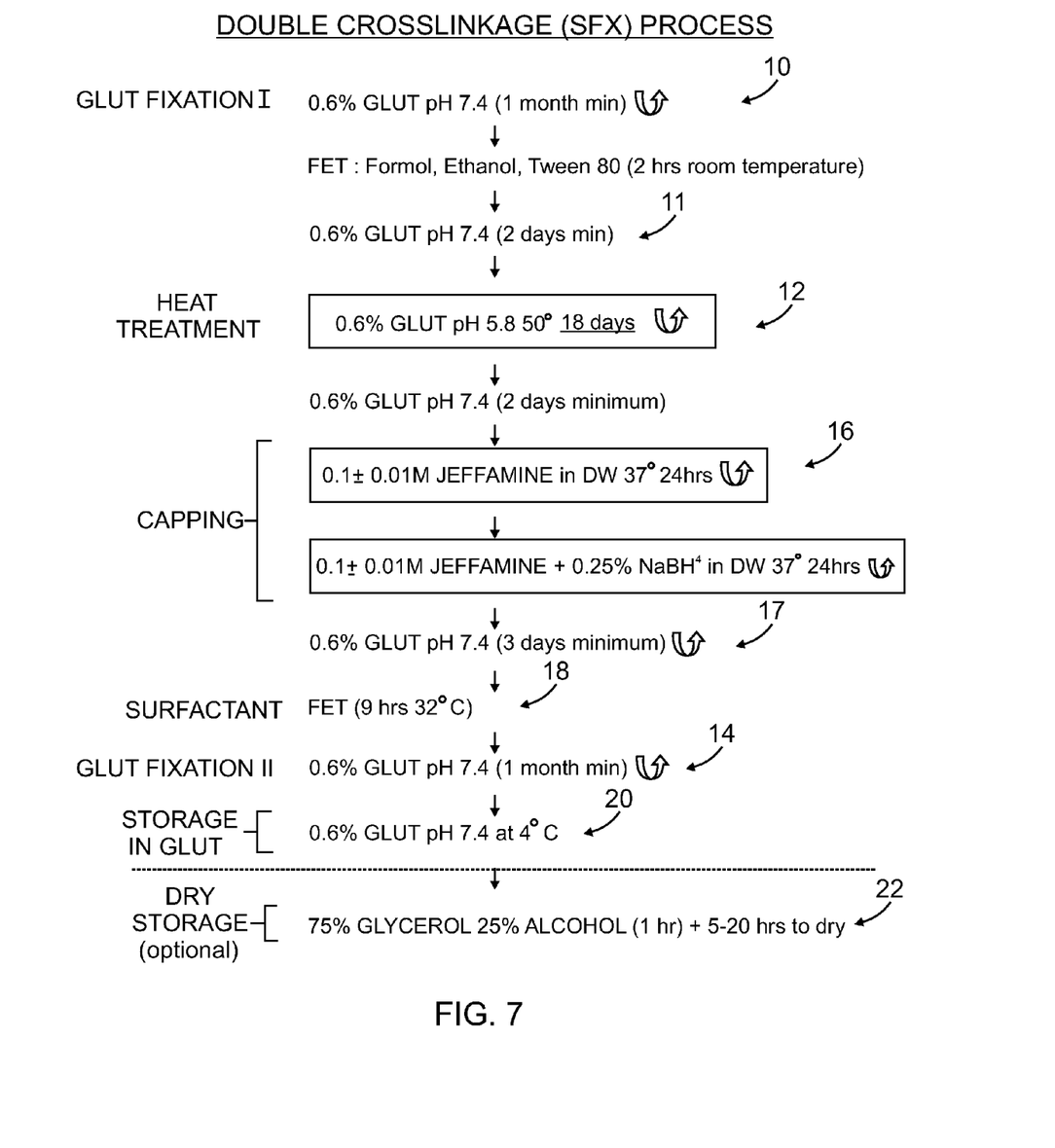
FIG. 7 is a summary of an exemplary double crosslinkage process described herein.

FIG. 7 is a flow chart showing an embodiment of the inventive process. The tissue is exposed to a 0.6% glutaraldehyde solution at pH 5.8 at 50° C. for 18 days 12, then 0.6% Glut at room temperature for at least 2 days 11. Capping/crosslinking with 0.1±0.01M Jeffamine in distilled water (DW) for 24 hours at 37° C., is followed by further exposure to Jeffamine under reducing conditions with sodium borohydride for 24 hours at 37° C. 16. This step 16 is followed by treatment with 0.6% Glut at pH 7.4 for at least 2-3 days 17 and then Surfactant (FET) for 9 hrs at 32° C. 18. Storage is done in 0.6% Glut at 4° C. 20, or optionally in a solution of 75% glycerol/25% ethanol 22.

EXAMPLES

Example 1

Calcification Mitigation—Rat Model

In order to evaluate the calcification mitigation properties of pericardial tissue treated in accordance with the method described herein ("SFX-treated"), animal feasibility studies were conducted. After rinsing of the samples in 0.9% NaCl to eliminate excess Glut, 18 samples/treatment (n=4/rat) were implanted subcutaneously on the back of 12 day old rats for 6 weeks (FIG. 3). These studies demonstrated that Jeffamine crosslinking/sodium borohydride treatment is superior to ethanolamine/sodium borohydride which is superior to the control group (Glut only) in mitigating the occurrence of calcification in tissue (0.1 vs 51.61 vs 103.1 μg/mg).

In all studies in rats, SFX-treated tissue demonstrated reduced variability in calcification data when compared to control tissue. Data from intramuscular implantation in rabbits were discarded because they were associated with too many variations.

Example 2

Aldehyde Crosslinking using Jeffamine and Sodium Borohydride of Glutaraldehyde-Fixed Tissue Bioprosthetic tissue was removed from 0.625% glutaraldehyde just after a heat treatment step, and stored in 0.6% Glut (pH 7.4) for 2 days. One liter of crosslinking solution was prepared containing 333 mM Jeffamine (Poly (propylene glycol) bis (2-aminopropyl ether), average M 230 (Aldrich ref. 406651) and 0.25% sodium borohydride in DW.

The capping solution was placed on an orbital shaker, then tissues (leaflets, pericardium) were placed in the solution with a ratio of 3 leaflets per 100 ml. The container was not completely sealed because hydrogen gas liberated by the chemical reaction with water could cause the container to explode. The orbital shaker was operated at between 60-80 rpm for 24 hours at 37° C. The tissue was removed and stored in 0.6% Glut solution for 2-3 days and then treated in the FET solution (formaldehyde, ethanol, Tween-80) for 9 hours at 32° C. before being stored in 0.6% Glut solution until implantation.

Example 3

Amino Group Crosslinking using a High Concentration of Dialdehydes at High Temperature As shown in FIG. 6, tissues were treated first at 50° for 6 days, then in 0.5M lysine for 24 hours at 37° C. with agitation. The FET treatment was applied either before or after lysine treatment.

The effect of lysine treatment is cumulative to the heat treatment, and FET further improves results. The place of FET could play a role with a preference when FET is after lysine treatment.

Example 4

Storage

Two storages processes have been developed:
1—Low concentration Glutaraldehyde Storage:

This is the preferred storage process for valves prepared using tissue treated according to the method described herein. Provided that certain conditions are respected, storage in glut does not enhance calcium mitigation. These conditions are storage in 0.6% Glut for at least 2 months and thorough rinsing before implantation.
2—No Glutaraldehyde Storage: Glycerol An alternative to avoid glutaraldehyde as a storage solution is to dehydrate the bioprosthetic tissue in a glycerol/ethanol mixture, sterilize with ethylene oxide, and package the final product "dry." This process is said to circumvent the potential toxicity and calcification effects of glutaraldehyde as a sterilant and storage solution. There have been several methods proposed to use glycerine, alcohols, and combinations thereof as post-glut processing methods so that the resulting tissue is in a "dry" state. The storage of heart valve tissue in glycerol was described by Parker et al. (Thorax 1978 33:638), but does not include any calcification mitigation techniques and does not describe any advantages. Also, U.S. Pat. No. 6,534,004 (Chen et al.) describes the storage of bioprosthetic tissue in polyhydric alcohols such as glycerol. However, neither of these methods addresses mitigating potential oxidation of the tissue. The recommended process was described in Edwards U.S. patent publication no. 2009-0164005.

While the invention has been described in terms of exemplary embodiments, it is to be understood that these examples are descriptive and are not meant to be limiting. Therefore, changes may be made within the appended claims without departing from the true scope of the invention.

The invention claimed is:

1. A method for preparing bioprosthetic implant tissue, comprising:
fixing a biological tissue with glutaraldehyde,
exposing said fixed tissue to a polyetheramine cross-linking agent under reducing conditions,
treating said exposed tissue with glutaraldehyde, and
storing said treated tissue in a terminal sterilization solution or further subjecting said treated tissue to a glycerol treatment solution.

2. The method of claim 1, wherein the fixing is conducted with 0.1 to 10 wt % concentration of glutaraldehyde at about 50° C. and pH 5.8 for 2 to 25 days.

3. The method of claim 1, wherein the exposing step is conducted in the presence of a reducing agent.

4. The method of claim 3, wherein the reducing agent is sodium borohydride.

5. The method of claim 1, wherein the polyetheramine cross-linking agent is delivered in water or a buffer solution.

6. The method of claim 1, wherein the polyetheramine cross-linking agent is at a concentration of 0.01M to 1M and the exposing is performed for a period of 1 hour to 7 days, at temperatures between 4° C. and 50° C., and at pH between 8 and 13.

7. The method of claim 6, wherein the polyetheramine cross-linking agent is at a concentration of 0.1M, and the exposing is performed for 48 hrs, at a temperature of 37° C., and at a pH 11.7.

8. The method of claim 4, wherein sodium borohydride is used as an adjunct to the polyetheramine cross-linking agent at a concentration between 0.05% and 1%, and the exposing is performed for a period of 1 hr to 3 days at a temperature between 4° C. and 40° C.

9. The method of claim 8, wherein the sodium borohydride is at a concentration of 0.25% and the exposing is performed for a period of 24 h at a temperature of 37° C.

10. The method of claim 1, wherein during the fixing step, the glutaraldehyde concentration is 0.6 to 10 wt. %, and the fixing is performed for 1 to 90 days, at a temperature from 37° C. to 75° C., at a pH of 5.4 to 6.8.

11. The method of claim 10, wherein during the fixing step, the glutaraldehyde concentration is 5%, and the fixing is performed for a time of 18 days, at a temperature of 52±2.5° C., at a pH of 5.8.

12. The method of claim 1, further comprising treating the fixed tissue in a surfactant solution thereby substantially eliminating phospholipids.

13. The method of claim 12, wherein the surfactant solution contains formaldehyde, ethanol and polyoxyethylene 20 sorbitan monooleate.

14. The method of claim 1, wherein said biological tissue is selected from the group consisting of bovine pericardium, porcine tissue, blood vessels, skin, dura mater, pericardium, small intestinal submucosa, tissue heart valves, ligaments, and tendons.

15. The method of claim 1, wherein said biological tissue is a native valve treated and mounted as a whole valve.

16. The method of claim 1, wherein the treated biological tissue is stored in the terminal sterilization solution and wherein the terminal sterilization solution is a glutaraldehyde solution of 0.1% to 0.6 wt. % concentration.

17. The method of claim 1, wherein the treated biological tissue is further subjected to the glycerol treatment solution and stored dry.

18. The method of claim 17, wherein the biological tissue is dehydrated after being further subjected to the glycerol treatment solution.

19. The method of claim 18, wherein the dehydrated tissue is sterilized in ethylene oxide.

20. A method of preparing bioprosthetic implant tissue comprising:
fixing a biological tissue with at least 0.2 wt. % glutaraldehyde at pH 5-6.8 between 45°-75° C. for 1 to 90 days;
exposing said fixed tissue to a polyetheramine cross-linking agent followed by reduction of Schiff base with $NaBH_4$,
treating said exposed tissue with about 0.6 wt. % glutaraldehyde and then treating with a surfactant;
wherein the foregoing steps are performed while stirring.

21. The method of claim 20, wherein the fixing is done at a temperature of 50° C. for 18 days.

22. The method of claim 20, wherein the treating said tissue with about 0.6 wt. % glutaraldehyde is performed for at least 1 month.

23. The method of claim 20, further comprising storing the tissue in 0.6% glutaraldehyde at 4° C. for at least 2 months after treating the tissue with the surfactant.

24. The method of claim 20, further comprising treating the tissue with a glycerol solution after treating the tissue with the surfactant.

25. The method of claim 1, wherein the fixing is performed before the exposing.

* * * * *